United States Patent [19]

Sekine

[11] Patent Number: 4,844,090
[45] Date of Patent: Jul. 4, 1989

[54] PENCIL TYPE HEART POTENTIAL WAVEFORM MEASURING DEVICE

[76] Inventor: Yukio Sekine, 7-102, 2-chome Minami-cho, Tsurugashima-machi Iruma-gun, Saitama-ken, Japan

[21] Appl. No.: 78,036

[22] Filed: Jul. 27, 1987

[30] Foreign Application Priority Data

Jul. 28, 1986 [JP] Japan .................. 61-114491[U]

[51] Int. Cl.[4] ................................. A61B 5/04
[52] U.S. Cl. ............................. 128/696; 128/639
[58] Field of Search .............. 128/696, 733, 800, 802, 128/902, 419 R, 421, 422, 639

[56] References Cited

U.S. PATENT DOCUMENTS

| | | | |
|---|---|---|---|
| 4,319,581 | 3/1982 | Cutter | 128/639 |
| 4,350,164 | 9/1982 | Allain, Jr. | 128/696 |
| 4,535,783 | 8/1985 | Marangoni | 128/696 |
| 4,635,646 | 1/1987 | Gilles et al. | 128/696 |

OTHER PUBLICATIONS

"Insta-Pulse", Sales Brochure, Biosig. Inc., 5471 Royalmount Ave., Montreal, Canada H4P 1J3, 9/78.

Primary Examiner—Francis Jaworski
Assistant Examiner—George Manuel
Attorney, Agent, or Firm—Roberts, Spiecens & Cohen

[57] ABSTRACT

In this pencil type heart potential waveform measuring device, a first electrode is provided at the tip of a substantially round bar-like pencil device body, a second electrode is separated from the above mentioned first electrode on the outer periphery of a gripping part of the pencil body, a memorizing device for memorizing heart potential waveforms induced from the first and second electrodes is provided within the pencil body and an output terminal for output of heart potential waveform signals memorized in the memorizing device is provided in the pencil body.

8 Claims, 5 Drawing Sheets

PENCIL TYPE HEART POTENTIAL WAVEFORM MEASURING DEVICE

FIELD OF THE INVENTION

This invention relates to heart potential waveform measuring devices and more particularly to a pencil type heart potential waveform measuring device which is convenient to carry and with which heart potential waveforms can be very easily measured.

BACKGROUND OF THE INVENTION

Generally a heart potential diagram is taken in a clinical diagnosis of a heart disease. Not only in the clinical diagnosis and prevention of a heart disease but also on the health control in the daily life, if a heat potential diagram can be taken promptly as required and waveforms catching abnormal heart muscles or irregular pulses are obtained, if will be very convenient.

There is already such portable heat potentiometer as a folder heat potentiometer wherein heart potential waveforms are recroded in a cassete tape. However, there have been defects that this folder heart potentiometer is so complicated to fit and so comparatively large in form and weight as to be a considerable burden to be carried by a patient and that, as the time when the fit of a heart occurs is not known and the fit is temporary, even if the folder heart potentiometer is fitted, there will be often nothing abnormal and no sufficient effect will be able to be obtained with the required toil.

Therefore, there is recently provided a small light heart potentiometer in which a semiconductor memory is contained and the above mentioned defects are improved. That is to say, this heart potentiometer is generally in the form of a disk having a proper thickness and provided with electrodes respectively on the upper and lower surfaces. In the use, as shown in FIG. 8, a heart potentiometer 31 is held with a right hand 19 and is pressed against such part to be measured as a breast. In this case, one electrode is contacted with the breast or the like and the other electrode is contacted with the palm of a hand to induce a heart potential. However, the form will be thin disk-like, an excess force may be applied to use it and a finger tip 19a will contact the breast. Therefore, there have been defects that the potential difference will reduce or vanish and a noise will mix in to make it difficult to measure accurate heart potential waveforms.

OBJECTS AND SUMMARY OF THE INVENTION:

The present invention is suggested in view of the above mentioned points and has it as an object to provide a pencil type heart potential waveform measuring device which is small and light and is convenient to carry and with which accurate heart potential waveforms can be very easily measured and caught.

That is to say, in order to attain the above mentioned object, the present invention comprises a first electrode provided at the tip of a substantially round bar-like pencil type device body, a second electrode separated from the above mentioned first electrode on the outer periphery of a gripping part of the above mentioned device body, a memorizing means provided within the above mentioned device body to memorize heart potential waveforms induced from the above mentioned first and second electrodes and an output terminal provided in the above mentioned device body to take out the heart potential waveforms memorized in the above mentioned memorizing means.

In this invention, the device is of a pencil type, is made small and light and is made easy to measure heart potential waveforms so that the measurement may be made positively.

DETAILED DESCRIPTION OF PREFERRED EMBODIMENTS

The present invention shall be explained in the following with reference to the drawings.

Figure 1:
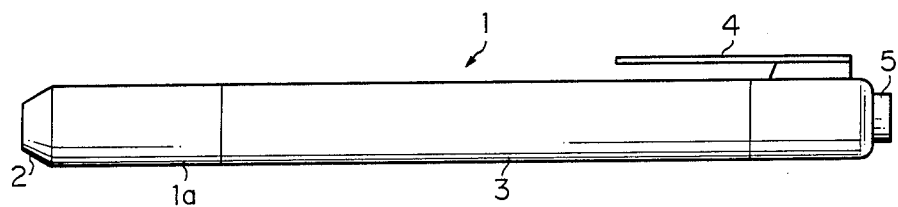
FIG. 1 is a side view of the first embodiment of the present invention.

FIG. 1 is a side view of the first embodiment of the present invention. A substantially disk-like first electrode 2 is provided at the tip of a hollow round bar-like pencil type body 1 made of an insulating synthetic resin or the like and a cylindrical second electrode 3 is provided in the gripping part on the outer periphery of the body 1 in separated relation from the first electrode 2. The first and second electrodes are silver chloride electrodes insulated from each other by an insulating part 1a. The flat shape of the first electrode 2 can be properly selected as required but is usually preferably made about 1 $cm^2$. so as to be positioned between the ribs to positively detect heart potential waveforms. The second electrode 3 is provided over the outer periphery so as to be able to secure a sufficient contact surface area when gripped by the hand of the user. By the way, in the above, the device body 1 may be polygonal.

Figure 2:
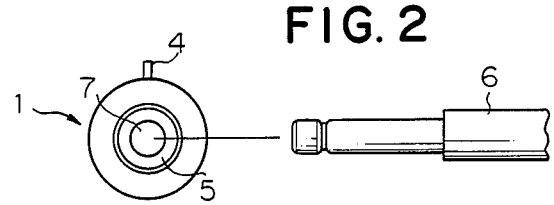
FIG. 2 is an explanatory view of an operating switch part.

Further, a pocket pin 4 is provided on the outer periphery at the end of the device body 1. A push type operating switch 5 of conventional structure is provided at the end remote from the first electrode 2. As shown in FIG. 2, an ouptut terminal 7 such as a female connector for taking out data in which a connecting terminal 6 such as a male connector can be removably fitted is provided in the center of operating switch 5.

Figure 3:
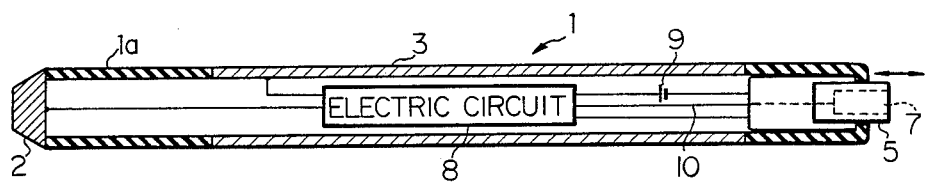
FIG. 3 is a schematic sectional view of an internal structure.

FIG. 3 shows the internal structure of a pencil type heart potential waveform measuring device. The first and second electrodes 2 and 3 are connected to an electronic circuit 8 provided within the device. The electronic circuit 8 is formed of various IC's incorporated in a printed substrate. A current source 9 such as a lithium battery for the electronic circuit is provided between electronic circuit 8 and operating switch 5 so that, when the operating switch 5 for switching the current source on and off is switched on, an electric current from the current source may be fed to the electronic circuit 8. A lead wire 10 for delivering an output is wired between the output terminal 7 and electronic circuit 8.

Figure 4:
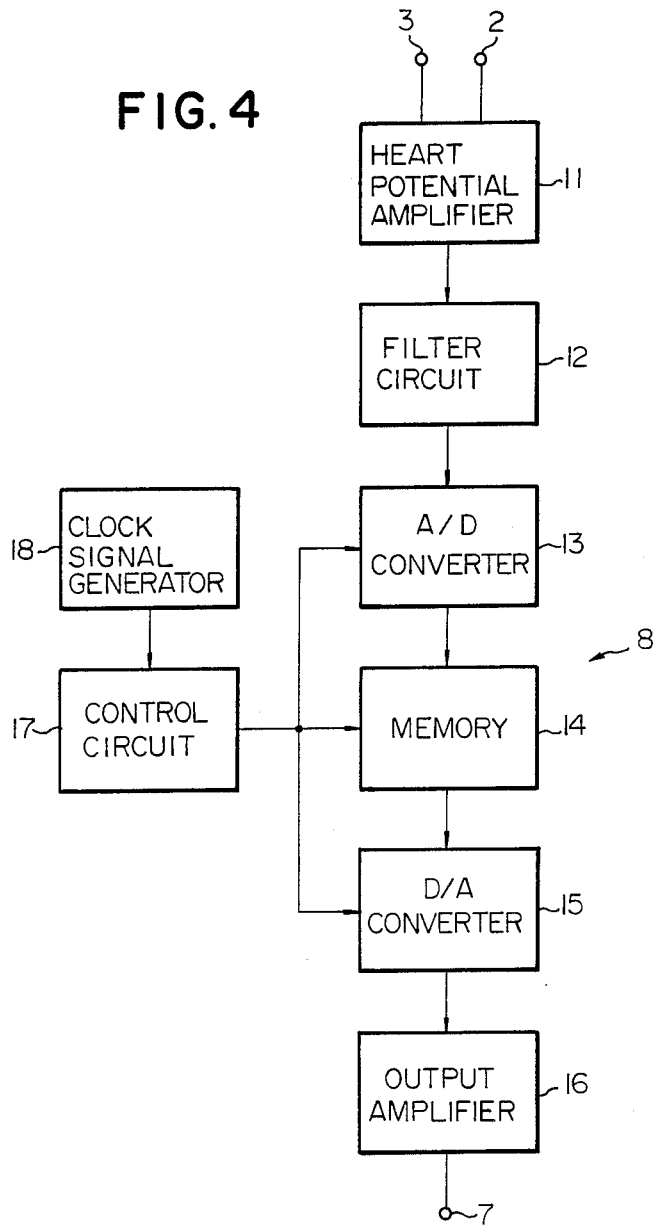
FIG. 4 is a basic block diagram of an electronic circuit of the present invention.

FIG. 4 shows a block diagram of a basic formation of the above mentioned electronic circuit 8. The reference numeral 11 represents a heart potential amplifier connected with the first and second electrodes 2 and 3, 12 represents a filter circuit to which the output of heart potential amplifier 11 is to be applied, 13 represents an A/D converter and 14 represents a memory such as a random access memory recording a heat potential waveform in the form of a digital signal. The current source 9 shown in FIG. 3 is applied as a backup current source to the memory 14 but another backup current source may be prepared. The reference numeral 15 represents a D/A converter, 16 represents an output amplifier connected to the output terminal 7 and 17 represents a control circuit controlling the A/D converter 13, memory 14 and D/A converter 15. The reference numeral 18 represents a clock signal generator generating a clock signal controlling the timing of the entire system.

The operation of the present invention shall be explained in the following.

The pencil type heart potential waveform measuring device of the present invention can be contained in a pocket of a suit or shirt by using the pocket pin 4, as it is small and light and is therefore convenient to carry.

Figure 5:
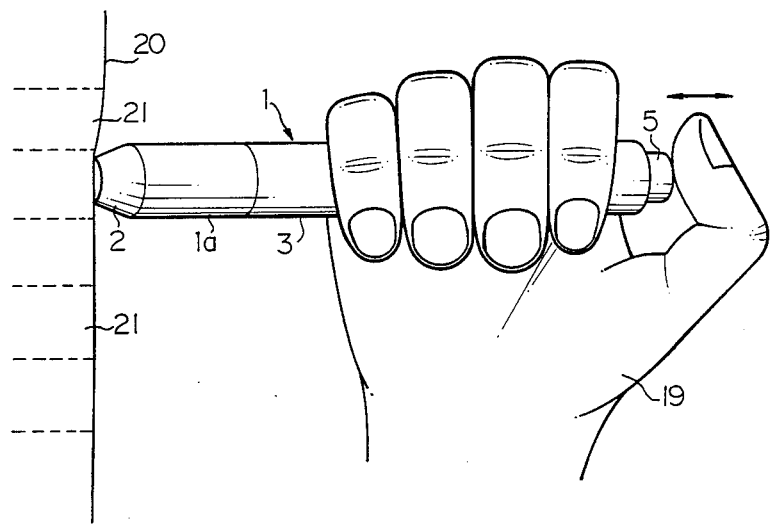
FIG. 5 show the embodiment in an operating state explaning view.

In using it, as shown in FIG. 5, the body 1 may be gripped, for example, with the right hand 19, the first electrode 2 may be brought into contact with a breast 20 of the user and the operating switch 5 may be pushed in to be switched on. As the second electrode 3 is provided on the outer peripheral surface of the device body 1, the area of contact with the right hand is large and, as the body 1 is applied substantially normal to the breast 20, the right hand 19 can be positively isolated from the breast and the fingers tip will not contact the breast. Therefore, it is not likely that the heart potential will reduce or vanish or a noise will mix in due to such contact.

The heart potential between the right hand and breast will be amplified by the heat potential amplifier 11, the signal will pass through the filter circuit, will have the frequency component above 200 Hz unnecessary for the heart potential measurement attenuated in the course, will be applied to the A/D converter to become a digital signal and will be memorized in the memory 14 so as to be able to be taken out as required.

That is to say, the digitalized heart potential waveform signal in the memory 14 will be again made an analog signal by the D/A converter 15 and the original heart potential waveform will be amplified by the output amplifier 16 and will be impressed on the output terminal 7. Therefore, if a display device such as a graphic printer is connected to output terminal 7, the heart potential waveform memorized in the memory 14 will be able to be taken out to be recorded.

By the way, the block diagram shown in FIG. 4 is of a basic formation. It is needless to say that a connecting condenser for removing direct current signals may be inserted between the first and second electrodes 2 and 3 and the heart potential amplifier 11 or an instant switch (not illustrated) for discharging the accumulated charge may be properly added to the connecting condenser.

Figure 6:
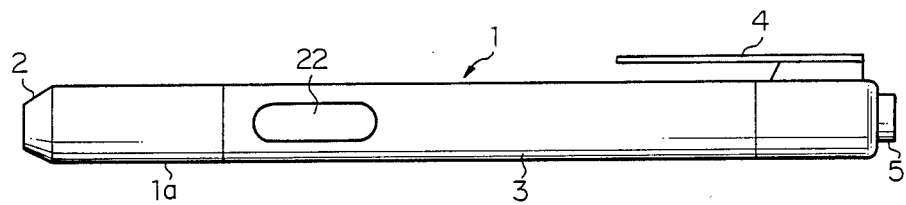
FIG. 6 is a side view of a second embodiment of the present invention.
Figure 7:
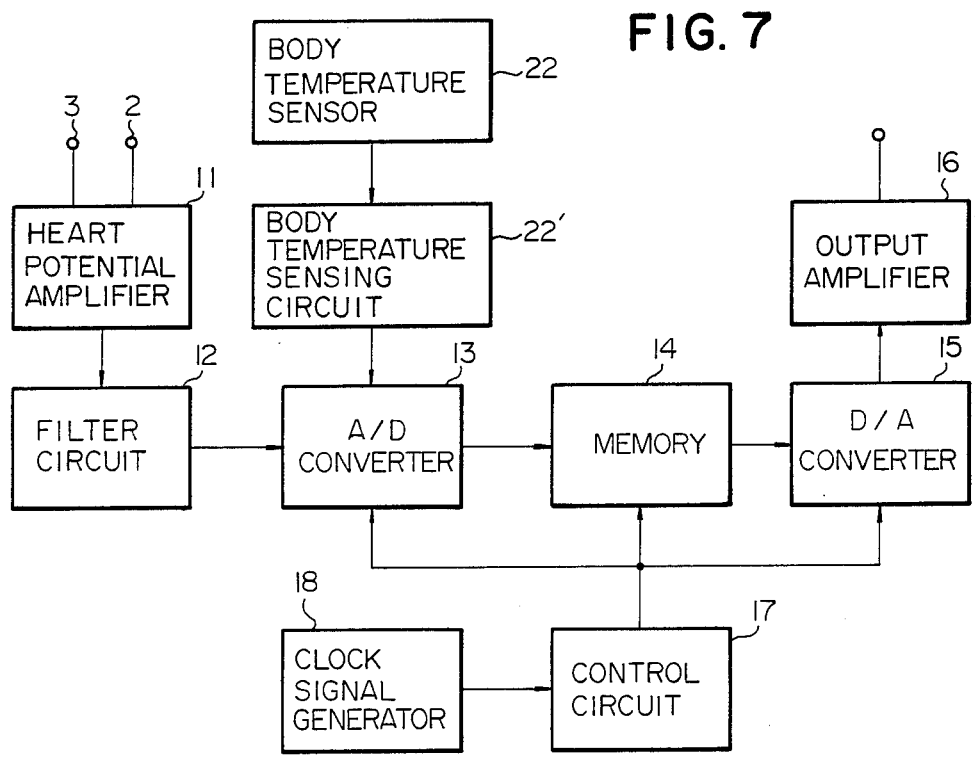
FIG. 7 is a basic block diagram of the same.
Figure 8:
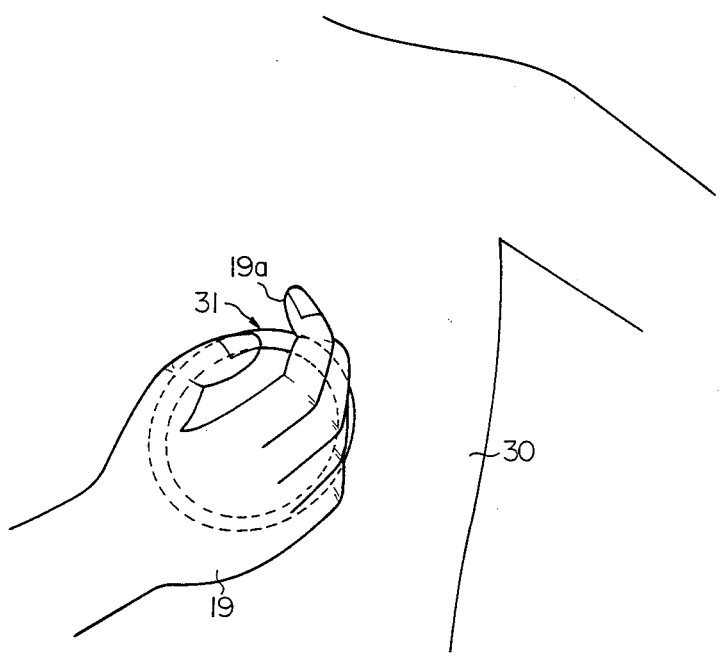
FIG. 8 is a diagrammatic illustration showing the use of a prior art example.

FIGS. 6 and 7 show the second embodiment of the present invention. In this embodiment, a body temperature sensor 22 is attached to the gripping part so that a body temperature signal may be obtained by a body temperature sensing circuit 22' from the output signal of the body temperature sensor 22. Therefore, the body temperature at the time of measuring the heart potential waveform can be measured and recorded as data. By the way, the other formations and functions are substantially the same as in the first embodiment, therefore the same reference numerals shall be respectively applied to the same components and the detailed explanation thereof shall be omitted.

As in the first embodiment, according to the present invention, the body is of a round bar-like pencil type, the first electrode of the body surface electrode is small and the second electrode is provided on the outer periphery of the body. Therefore this heart potential waveform measuring device is small and light, is adapted to be carried, the device body is gripped so that the body surface electrode at the tip may be contacted with a breast and, in such case, the gripping hand will not contact the breast or the like and therefore the precision of measuring the heart potential waveform will be high.

As the body is round bar-like, the body surface electrode part can be easily slipped onto a breast from outside a suit through an unbuttoned shirt so that the measurement may be easy.

It is apparent that, in this invention, working modes different in a wide range can be formed on the basis of this invention without departing from the sprit and scope of the invention. This invention is not restricted by its specific working mode except as limited by the appended claims.

What is claimed is:

1. A pencil type heart potential waveform measuring device comprising an elongated body having opposite end portions, a first electrode mounted on said elongated body at one of said end portions adapted to be placed into contact with the body of a patient as the elongated body extends upright from the body surface of the patient, a second electrode on said elongated body in spaced relation from the first electrode, said second electrode being constructed to extend over and form a portion of the outer periphery of said elongated body and thereby constitute a gripping means adapted for the hand of a user in application of the elongated body in contacting the body of the user, the contact of the first electrode with the body of the user in the region of the heart of the user and the contact by the hand of the user with the second electrode producing signals indicative of heart potential waveforms, memory means in said elongated body connected to said first and second electrodes for memorizing the signals received from said first and second electrodes, and an output terminal connected to said memory means and accessible from outside said elongated body to provide the signals memorized in said memory means.

2. A device as claimed in claim 1 wherein said elongated body comprises an insulating element interposed between said first and second electrodes.

3. A device as claimed in claim 2 wherein said insulating element and said second electrode comprise adjoining tubular elements.

4. A device as claimed in claim 1 comprising a power source for said memory means, and means accessible from outside the elongated body for activating said power source.

5. A device as claimed in claim 4 wherein said means for activating said power source comprises an operating switch to which said second electrode is connected.

6. A device as claimed in claim 5 wherein said operating switch is movably supported at the other of said end portions of said elongated body.

7. A device as claimed in claim 1 comprising temperature sensing means on said elongated body adapted for being contacted by the hand of the user when gripping said gripping means to measure the temperature of the body of the user.

8. A device as claimed in claim 7 wherein said temperature sensing means is electrically connected to said memory means.

* * * * *